United States Patent [19]
Lemmen et al.

[11] Patent Number: 5,993,754
[45] Date of Patent: Nov. 30, 1999

[54] STERILIZATION VESSEL IN THE FORM OF A CASSETTE

[75] Inventors: Marcel Lemmen, Mississauga; Chris Wu, Toronto, both of Canada

[73] Assignee: SciCan, Canada

[21] Appl. No.: 09/056,473

[22] Filed: Apr. 7, 1998

[30] Foreign Application Priority Data

Apr. 7, 1997 [DE] Germany ............................ 197 14 298

[51] Int. Cl.[6] .................................................... A61L 2/00
[52] U.S. Cl. ......................... 422/293; 422/296; 422/297; 422/300
[58] Field of Search ..................................... 422/293, 292, 422/295, 296, 297, 300; 49/477.1; 137/384

[56] References Cited

U.S. PATENT DOCUMENTS

| | | | |
|---|---|---|---|
| 4,999,165 | 3/1991 | Calabra et al. | 422/296 |
| 5,424,047 | 6/1995 | Zwingenberger et al. | 422/296 |
| 5,571,476 | 11/1996 | Newman | 422/26 |
| 5,795,552 | 8/1998 | Corby et al. | 422/294 |
| 5,846,484 | 12/1998 | Scarborough et al. | 422/28 |

*Primary Examiner*—Krisanne Thornton
*Attorney, Agent, or Firm*—Chapman and Cutler

[57] ABSTRACT

An adapter for a sterilization cassette type apparatus in the form of a cassette is mounted in the cassette clamping members and is constructed as a fluid distributor with a plurality of funnel-shaped receiving openings each having a cylindrical outer wall for receiving of medical or dental instruments to be cleaned and/or sterilized.

12 Claims, 2 Drawing Sheets

STERILIZATION VESSEL IN THE FORM OF A CASSETTE

BACKGROUND OF THE INVENTION

1. Field of Invention

The invention relates to a sterilization chamber in the form of a cassette slidable into a sterilization apparatus and having fluid inlet and venting ports, with a bottom tray and an upper lid for the efficient holding of medical and/or dental instruments with fluid channels to be cleaned and/or sterilized.

2. Description of the Related Art

As experience has shown, there are special difficulties in cleaning and/or sterilizing long-extended medical and/or dental instruments with fluid channels, such as hand and angle pieces, after their use, to make them germ-free for the next usage. The cleaning and/or sterilization fluid must, namely, be led through all the cavities and channels in a sufficient manner.

A further difficulty is presented from the fact that instead of autoclaves having large-volume sterilization chambers, are therewith consuming much energy, there are now in use sterilization apparatuses the sterilization spaces of which are constructed as two-part cassettes slidable into the sterilization apparatus, having a bottom tray and an upper lid, the low volume of which makes possible an economical working requiring little time.

Thus, from EP 0 638 297 A1 is known a sterilization apparatus for the insertion of such sterilization vessels in the form of cassettes which have several adapters for the reception of elongated medical and/or dental instruments with fluid channels. Each of these adapters contains a connecting pin which is constructively adapted to the construction of the instruments. On the end facing away from the instrument, each adapter is constructed so that it can be easily detachable affixed to the back wall of the lower part of the cassette, for which purpose a rest lug is provided which cooperates with annular groove on the back wall of the lower part of the cassette. In each adapter there is present a slidable switching plunger which is activated by the sliding of an instrument onto the adapter against the force of a spring, and in the process frees the needed fluid channels. Such a construction is complicated and requires provisions on the cassette itself, so that cassettes of different construction type become necessary, and cassettes already present cannot subsequently be equipped with such adapters.

SUMMARY OF THE INVENTION

Accordingly, it is an object of the present invention to create an inexpensive adapter device comprising few components, with which such a cassette serving as a sterilization vessel for the holding of instruments having cavities and fluid channels are equipped in a simple manner, operating in a simple manner, secure in operation, without the cassettes themselves having to be altered or especially constructed.

In order to achieve these objects, the adapter is constructed as a fluid distributor detachable installable in the cassette, transversely to its longitudinal extent, which distributor is fluid-connected with a fluid inlet port detachable installed in a fluid channel inside the cassette.

According to a further feature of the invention both the distributor and also the fluid inlet port have clamps for providing a detachable connection with the cassette and of its fluid channel. For this the fluid distributor of the invention is constructed as a building slab, approximately rectangular in cross section, on the base surface of which the clamps are molded. On the front surface of the slab and at a right angle thereto the instrument holders are molded, which in each case have a funnel-shaped reception opening and a cylindrical outer wall. In this arrangement the fluid inlet port has a support plate having a spring clamp and an fluid-conducting means fitting into the fluid-conducting seal of the cassette, which means communicates with a tube connection.

The construction of the adapter device according to the invention provides the cleaning and sterilizing of instruments having openings and provided with fluid channels, such as dental hand instruments, surgical endoscopy instruments, medical tube material and the like are substantially facilitated. Also, the use of the adapter device according to the present invention, especially the use of an adapter detachable connected with the cassette by means of a clamping connection, installable transversely to the longitudinal extent, which has several reception openings for the pluggable insertion of instruments to be cleaned and sterilized, allows the cassettes on hand and also cassettes newly acquired to be re-equipped in a simple manner for the sterilizing of elongated instruments or for the sterilizing of the usual medical instruments having a small longitudinal extent, such as syringes and the like, and can be used equally well after the removal of the adapter device.

BRIEF DESCRIPTION OF THE DRAWINGS

The above and other objects, features, and advantages of the present invention will be described by reference to the accompanying specification and drawings, in which.

DETAILED DESCRIPTION OF THE PREFERRED EMBODIMENTS

Figure 1:
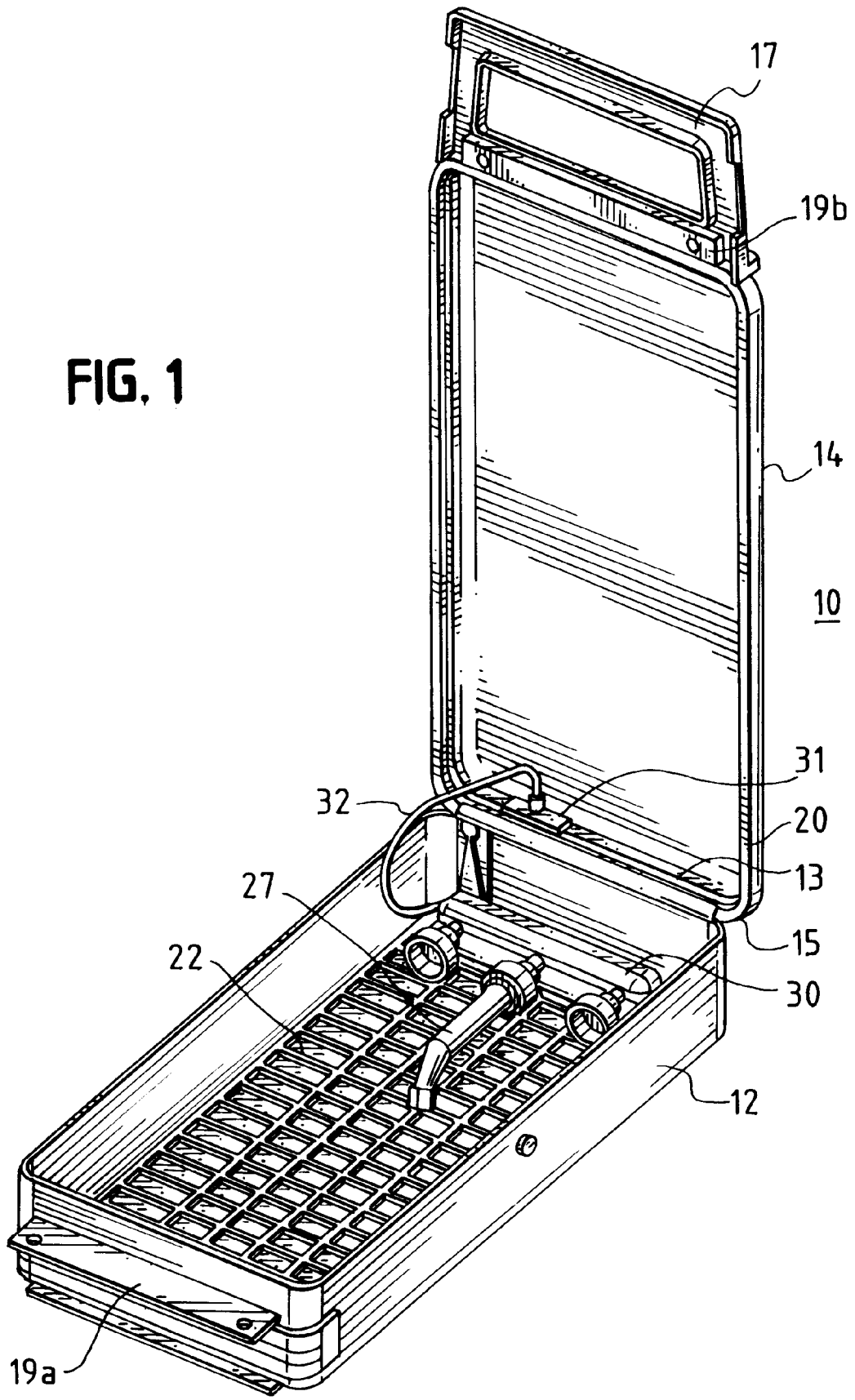
FIG. 1 shows in perspective a cassette consisting of a bottom tray and upper lid as a sterilization vessel for medical and/or dental instruments with an installed multi-part adapter device according to the invention.
Figure 4:
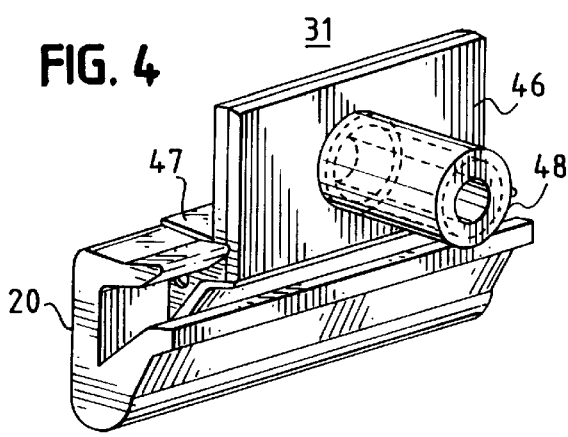
FIG. 4 shows in perspective the fluid inlet port of the adapter device according to FIG. 1.

A sterilization vessel generally in the form of a rectangular cassette 10, generally designated slidable into a sterilization apparatus (not shown), is shown in FIG. 1. The cassette 10 includes a bottom tray 12 and an upper lid 14, which are joined with one another by a hinge 15. By means of a hand grip 17 on the upper lid 14, the bottom tray and the upper lid can be closed pressure-tight with one another before the sliding into the sterilization apparatus (not shown). Serving this purpose is a lock 19a/19b applied in part to the bottom tray and in part to the upper lid, as well as a seal 20 lining the border of the upper tray 14, the non-equilateral, roughly U-shaped cross section of which is clearly seen in FIGS. 4 and 5. On the base of the tray of cassette 10 there lies a grid 22 as support for the medical and/or dental instruments to be sterilized. The cassette 10 has, further, inlet and outlet apertures for the entry and the exit of the cleaning and/or sterilization fluid, for example steam. The cassette described is known and is available on the market.

Figure 2:
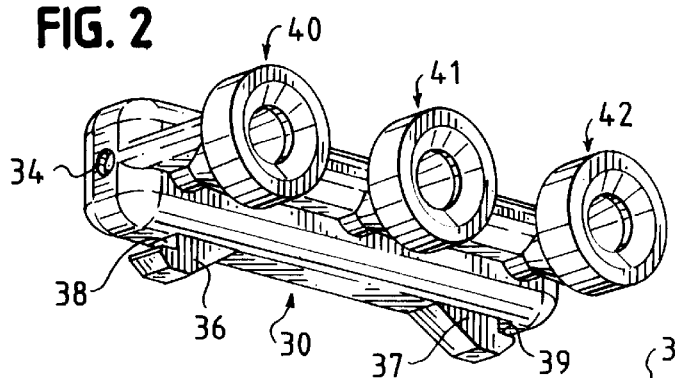
FIG. 2 shows in perspective, the fluid distributor of the adapter device according to FIG. 2.
Figure 3:
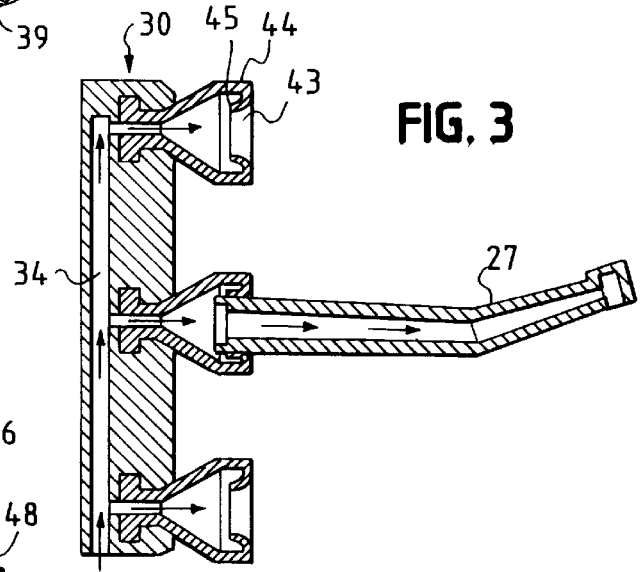
FIG. 3 shows a section through the fluid distributor according to FIG. 2.

For the functionally proper reception and cleaning of instruments with cavities and fluid channels, such as, for example, dental angle pieces 27, an adapter device is provided, which consists of a fluid distributor 30, a fluid inlet port 31 and a tube 32 fluid-connecting the two parts. The fluid distributor 30 and the fluid inlet port 31 are represented in detail in FIGS. 2 to 5. The fluid distributor 30, as it is represented in FIGS. 2 and 3, is a block-shaped body made of a heat-resistant plastic material, with a central fluid channel 34. On the side of the fluid distributor 30 facing the grid 22, that is its base surface, there are molded-two integral abutments 36 and 37 spaced from one another and aligned with respect to one another. They are installed in the cassette (see FIG. 1) and grip bars of the grid 22 with their outer surfaces 38 and 39. On the side surface arranged at a right angle to the base surface of the fluid distributor there are molded three instrument holders 40, 41 and 42, the central openings of which communicates with the fluid channel 34 (see FIG. 3.)

As shown in FIGS. 2 and 3, the instrument holders are constructed in funnel form and have in each case a funnel-shaped reception opening 43 and a cylindrical-shaped outer wall 44, which is constructed elastic in each case and is reshaped inward into a clamping surface 45. In this manner, in the installing of an instrument, such as, for example, the angle piece 27, a fluid-tight connection between the instrument holder and the instrument is achieved (see FIG. 3.) Because of the elastic construction of the instrument holders, instruments of different diameter can be inserted equally well. The fluid inlet port 31 comprises on one surface a support plate 46 of stainless steel, onto which a curved spring clamp 47 is molded and it carries, on the opposite surface, a tube connector 48. To one side face of the support plate 46 there is molded an angular fluid-conducting means 52 which, along with the seal 20, forms a fluid channel 63 which is connected, through the fluid channel 54 in the support plate 46, with the opening 49 of the tube connection 48; (see FIG. 5).

Figure 5:
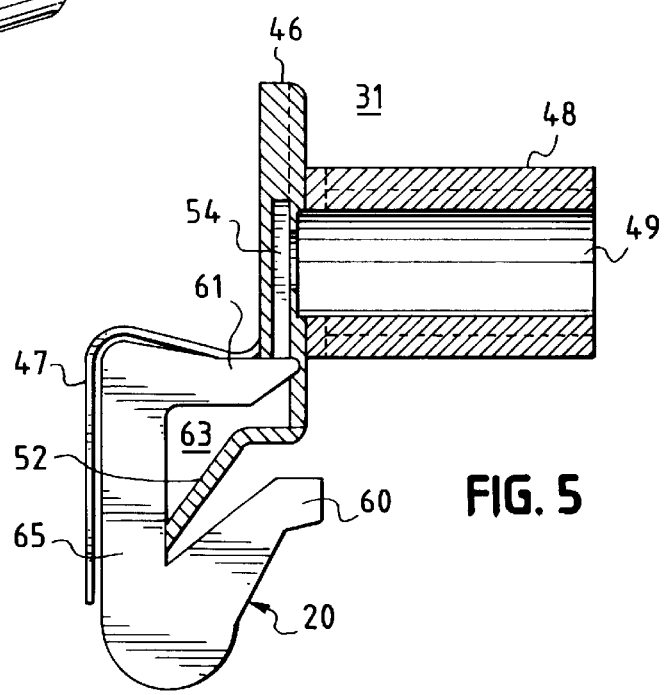
FIG. 5 shows a section through the fluid inlet port according to FIG. 4.

In the space enclosed by the sides 60 and 61 of the seal 20 and by the lower edge 13 of the upper lid 14 of the cassette 10, in cassettes of this type the supplying of the fluid or fluids occurs. By placing the described fluid inlet port 31 on the upper lid 14 of the cassette 10, for example in the region of the hinge 15 (as shown in FIGS. 1 and 5), the side 61 and the internal fluid channel 63 of the seal 20 are tightly sealed, so that a fluid connection to the channel 54 and therewith to the tube connector 48 is established. Over the tube 32, which likewise is made of a heat-resistant plastic material and carries on the ends clamps connecting the aperture of the fluid channel 34 of the fluid distributor and the tube connector 48, takes place the injection of the fluid over the fluid distributor 30 to the instruments inserted into the instrument holders 40 to 42, shown in FIG. 3 as the angle piece 27. Since the surfaces facing one another, both of spring and insert flange and also of fluid-conducting seal, are designed to fit closely with one another, there arises a fluid-tight connection between the described components connected with each another. In consequence of the chosen type of fluid connection and the function of the device described is maintained even when only one instrument is inserted into the fluid distributor, as shown in FIG. 1.

The operating of the cassette as sterilization vessel, there, is in no way hampered or in any manner unfavorably affected by the adapter device described. The described clamping connections of fluid distributor and fluid supply make possible an altogether simple installation and removing of the adapter device.

We claim:

1. A sterilization vessel in the form of a cassette slidable into a sterilization apparatus, comprising:

a bottom tray for holding articles to be sterilized;

a upper lid for placement over said bottom tray;

a fluid-conducting seal disposed along the edge of said lid having an internal fluid channel; and an adapter forming a fluid distributor having at least one article holder releasably mounted in the bottom tray with a fluid inlet port detachably mounted in the upper lid in communication fluid with the channel, and a connector providing fluid communication between the inlet port and the fluid distributor.

2. The sterilization vessel according to claim 1, wherein the fluid distributor including clamping means for detachable connection with the bottom tray.

3. The sterilization vessel according to claim 1, wherein the fluid distributor is generally rectangular in cross section, having a channel with an opening on one side of the distributor, and the article holders are formed at a right angle to a front surface of the distributor.

4. The sterilization vessel according to claim 2, wherein the clamping means of the fluid distributor are integral parts of the fluid distributor corresponding to assigned bars of a grate or rack installed in the bottom tray.

5. The sterilization vessel according to claim 1, wherein the fluid inlet port includes a tube connector arranged on a support plate, and a fluid conducting means fitting into the fluid-conducting seal of the upper lid forming a fluid connection with the connector.

6. The sterilization vessel according to claim 5, wherein the fluid inlet port includes clamping means for detachable connection with the seal.

7. The sterilization vessel according to claim 2, wherein the fluid distributor is generally rectangular in cross section, having a channel with an opening on one side of the distributor, a base surface with clamping means and a front surface on which the article holders are formed at a right angle thereto.

8. The sterilization vessel according to claim 7, wherein the clamping means of the fluid distributor are integral parts of the fluid distributor corresponding to assigned bars of a grate or rack installed in the bottom tray.

9. The sterilization vessel according to claim 3, wherein the article holders having a frustoconical receiving opening and a cylindrical outer wall.

10. The sterilization vessel according to claim 3, wherein the fluid inlet port comprises a connector arranged on a support plate, and a fluid conducting means fitting into the fluid-conducting seal of the upper lid forming a fluid connection with the connector.

11. The sterilization vessel according to claim 10, wherein the support plate is connected to the seal by a spring clamp.

12. The sterilization vessel according to claim 11, wherein the support plate is a flat plate, and all surfaces facing one another, including a surface of the spring clamp, a surface of the fluid-conducting means and a surface of the fluid conducting seal, form fluid tight interfaces.

* * * * *